United States Patent [19]

Heffernan et al.

[11] Patent Number: 4,885,932
[45] Date of Patent: Dec. 12, 1989

[54] DETERMINATION OF CLEANLINESS LEVEL OF FOAM RESERVOIR

[75] Inventors: Mary B. Heffernan, Encinitas, Calif.; Kenneth A. Norton; Bruce Cowger, both of Corvallis, Oreg.

[73] Assignee: Hewlett-Packard Company, Palo Alto, Calif.

[21] Appl. No.: 72,081

[22] Filed: Jul. 10, 1987

[51] Int. Cl.$^4$ ............................................. G01N 11/00
[52] U.S. Cl. ........................................ 73/53; 73/64.4
[58] Field of Search ........... 73/64.4, 53, 61 R, 61.1 R, 73/60.1

[56] References Cited

U.S. PATENT DOCUMENTS

| | | | |
|---|---|---|---|
| 3,060,318 | 10/1962 | Ouvrard | 73/53 |
| 3,618,374 | 11/1971 | Miller | 73/64.4 |
| 3,913,384 | 10/1975 | Furuya et al. | 73/53 |
| 4,269,627 | 5/1981 | Hwang | 524/159 |
| 4,812,492 | 3/1989 | Eckers et al. | 524/190 |

Primary Examiner—Hezron E. Williams
Attorney, Agent, or Firm—Roland I. Griffin

[57] ABSTRACT

The cleanliness in foams used as ink reservoirs and ink delivery systems in ink-jet printing is determined by at least one of two methods. In the first method, the amount of non-volatile residues is measured. An amount of NVRs of less than about 0.2 wt/wt % is sufficient to provide adequate ink fluid properties. In the second method, the surface tension is measured for ink vehicle prior to and following exposure to the foam. For inks formulated for specially-coated paper printing, so long as the surface tension following exposure to the foam is at least about 40 dyne/cm, then adequate ink fluid properties are assured. For inks formulated for plain paper printing, so long as the drop in surface tension is less than about 7 dyne/cm as compared to ink vehicle not so exposed, then adequate ink fluid properties are assured.

17 Claims, No Drawings

DETERMINATION OF CLEANLINESS LEVEL OF FOAM RESERVOIR

TECHNICAL FIELD

The present invention is related to ink-jet printing cartridges having foam reservoirs for storing ink, and, more particularly to means for ensuring that the foam reservoir is clean enough for use and will thus not contaminate the ink subsequent to loading ink therein.

BACKGROUND ART

In one variety of ink-jet printing cartridges, a foam is used as a reservoir to store the ink and to permit egress of the ink to the printhead on demand for printing.

The foam is typically a polyether-type polyurethane which is reticulated (the cell walls being blown out to provide even flow of ink therethrough) and felted (compressed to $\frac{1}{3}$ of its height to increase its density). An example of such a foam is available from Scotfoam (Eddystone, PA) under the trade designation SCOTFELT.

While the foam is ordinarily cleaned by the vendor following cutting to size, it is necessary to determine whether the foam is nevertheless at the proper level of cleanliness for use in the ink cartridge so as not to contaminate the ink and affect its fluid properties.

DISCLOSURE OF INVENTION

In accordance with the invention, a process is provided for determining the level of cleanliness of foam reservoirs for ink-jet cartridges. For inks formulated for specially coated papers, at least one of two tests, determination of non-volatile residue (NVR) levels and determination of surface tension, indicate the level of cleanliness of the foams. For inks formulated for plain paper, determination of surface tension is of primary importance; the determination of NVR levels may be done merely to ensure that the dye of the ink will not be decomposed by the NVRs.

The determination of non-volatile residues involves exposing the foam to a solvent which extracts the residues without attacking the foam. The solvent is then evaporated and the amount of residue remaining is weighed and compared with the starting weight of foam extracted. The weight of residue contributed by the solvent is subtracted from the weight of foam residue. An amount of less than about 0.2 wt/wt% of NVR in the foam has been found to ensure appropriate cleanliness level therein for specially-coated papers. For plain paper printing, this value is taken in conjunction with the surface tension test; if a good surface tension is obtained, then an NVR value of less than about 0.2 wt/wt% ensures that the ink's dye will not be decomposed by the non-volatile residues.

The determination of surface tension is accomplished by soaking the foam in the vehicle used to prepare the ink. A measurement of surface tension is made prior to the soaking and again thereafter. For inks formulated for specially-coated paper, the final surface tension should be greater than about 40 dyne/cm. At this value, the foam is sufficiently clean for use as an ink-storage reservoir. For inks formulated for plain paper, the drop in surface tension should not be greater than about 7 dyne/cm.

For inks formulated for printing on specially-coated papers, at least one of the foregoing steps is sufficient to ensure that the foam has the appropriate cleanliness to store ink. Both steps may be followed for a cross-check. For inks formulated for printing on plain paper, the surface tension measurement is the more critical determination of cleanliness level, with the NVR measurement being used to ensure that the dye in the ink will not be decomposed by the presence of NVRs.

BEST MODES FOR CARRYING OUT THE INVENTION

Two tests are performed on each lot of foam reservoirs received from the manufacturer: weight percent of non-volatile residues (NVR) and surface tension of ink vehicle after exposure to foam. For inks formulated for specially-coated papers, each test alone is sufficient to indicate the level of cleanliness of the foam and the resulting fluid properties of ink stored therein. The fluid properties of primary interest include the surface tension of the ink, its viscosity, its pH, and its electrical conductivity. For inks formulated for plain paper, the cleanliness level of the foam is primarily determined by the surface tension test.

% NVR. The foam is continuously extracted for several hours, typically 6 to 24 hours, in a solvent which is non-azeotropic and non-polar. Examples of suitable solvents include halo-hydrocarbons, such as 1,1,2-trichloro-1,2,2-trifluoroethane, and hydrocarbons, such as hexane.

The extraction is done in a Soxhlet or other extraction apparatus for a sufficient time to ensure substantially complete extraction. It appears that there are about seven components that comprise the non-volatile residues. Of these components, the most concern is directed to the presence of any surfactants.

In the procedure, the foam is weighed prior to extraction. The NVRs are then extracted from the foam, as above, and the solvent is poured into a container. The solvent is evaporated, preferably at room temperature, and transferred to a weight vial when the solvent is sufficiently reduced in volume. The solvent is then evaporated to dryness, and the vial weighed. The weight of the vial is compared to its weight prior to receiving the solvent.

A blank of the solvent is concurrently run as above to determine the level of NVR in the solvent. The amount of NVR from the extracted foam is then adjusted by subtracting the amount of NVR in the solvent therefrom. The weight of the residue is then compared to the weight of the foam prior to extraction to determine the NVR value.

It has been found that the amount of NVR in the foam should be less than about 0.2 wt/wt%. For inks formulated for specially-coated paper, this level of NVR is sufficient to ensure that the foam is clean enough so as to not contaminate the ink and thereby adversely affect its fluid properties. For inks formulated for plain paper, this level of NVR, in combination with a suitable result from the surface tension test, is sufficient to ensure that the foam is clean enough.

Surface tension. The foam is soaked in the vehicle used to prepare the ink. As is well-known, the ink comprises a vehicle and a colorant (dye). The vehicle typically comprises water and/or one or more glycols, as is also well-known, and thus the composition of the vehicle does not form a part of this invention.

An accelerated soaking is done. For example, the surface tension results of soaking at 60° C. for four days can be correlated with confidence to the surface tension of the ink after soaking at room temperature for 1.5 years (the shelf life of the foam). The surface tension of the vehicle is measured prior and subsequent to the soaking. As an example, 25 ml of the vehicle is injected into the foam. At the end of the soak time, the foam is squeezed to obtain a sufficient quantity of vehicle for the surface tension test.

The surface tension test may comprise any of the well-known tensiometer tests, such as the duNouy ring test, which give an apparent measure of surface tension, and a bubble test, which gives a true measure of surface tension. An example of equipment suitable for the latter test is a fluid surface tensiometer available from Chem-Dyne Corp. (Milwaukee, WI) under the trade designation SENSADYNE 5000.

For inks formulated for specially-coated paper, it has been found that so long as the measured surface tension after soaking is at least about 40 dyne/cm, then the foam is clean enough to be used to store ink therein. For inks formulated for plain paper, it has been found that so long as the drop in surface tension between the initial value and the value after soaking is less than about 7 dyne/cm, then the foam is clean enough.

The drop in surface tension is affected by the presence of surfactants, which should be removed in the cleaning process. Such surfactants may comprise 5 to 50% of the total NVR present in a foam. If the surfactant is not adequately removed, then the ink surface tension will drop in the pen over time and adversely affect the fluid properties of the ink.

INDUSTRIAL APPLICABILITY

The process of the invention is suitably employed to determine the cleanliness level of foam reservoirs used in ink-jet cartridges prior to filling of ink.

EXAMPLES

Known quantities of surfactants were added to inks and the negative head/capillary force of the pens was examined. A nominal acceptance level of surfactant was determined as well as a cut-off for acceptable surface tension of the ink.

Foam samples having a known NVR were injected with known quantities of dry residue collected from previous samples ("spike NVR") to give a total NVR ("total in"). After extraction ("total out"), the percent recovery of the spiked material was measured. The results are listed in the Table below (all weights are in grams).

TABLE

| Run | Foam NVR | Spike NVR | Total in | Total out | % Recovery |
| --- | --- | --- | --- | --- | --- |
| 1 | 0.0097 | 1.6713 | 1.6810 | 1.6496 | 98 |
| 2 | 0.0097 | 1.2892 | 1.2989 | 1.3103 | 101 |
| 3 | 0.0097 | 0.6528 | 0.6625 | 0.6679 | 101 |
| 4 | 0.0097 | 0.6775 | 0.6872 | 0.6923 | 101 |

The Table shows that the extraction efficiency of the NVR test is essentially 100%. Thus, essentially all of the NVR is recovered.

Thus, there has been provided a method of determining cleanliness level in foams used as ink reservoirs and ink delivery systems in ink-jet printing. It will be appreciated by those of ordinary skill in the art that changes and modifications of an obvious nature may be made. All such changes and modifications are considered to fall within the spirit and scope of the invention, as defined by the appended claims.

What is claimed is:

1. A method of determining cleanliness level in foams used as ink reservoirs and ink delivery systems in ink-jet printing to ensure removal of contaminants from said foam so as to provide ink stored in said foam with at least adequate ink fluid properties, said method comprising performing at least one of the following procedures:
   (a) determining whether the amount of non-volatile residues is greater or less than about 0.2% by weight; and
   (b) measuring whether surface tension of ink vehicle prior to and following exposure to said foam and determining whether the measured value of surface tension of ink vehicle following exposure to said foam is at least equal to or less than about 40 dyne/cm or whether the drop in surface tension of ink vehicle so exposed is greater or less than about 7 dyne/cm, with adequate ink fluid properties being associated with (1) an amount of non-volatile residues of less than about 0.2% by weight, (2) a final measured value of surface tension of at least about 40 dyne/cm for inks formulated for specially-coated paper, or (3) a drop in surface tension of less than about 7 dyne/cm for inks formulated for plain paper.

2. The method of claim 1 wherein the amount of non-volatile residues is determined by the following procedure:
   (a) weighing at least one foam;
   (b) extracting said at least one foam in a solvent capable of extracting said non-volatile residues without attacking said foam;
   (c) evaporating said solvent and determining the weight of the residue remaining; and
   (d) comparing said weight with the weight of said at least one foam that was extracted to determine whether said amount is greater than or less than about 0.2% by weight.

3. The method of claim 2 wherein said solvent is non-azeotropic and non-polar.

4. The method of claim 3 wherein said solvent is selected from the group consisting of halo-hydrocarbons and hydrocarbons.

5. The method of claim 4 wherein said solvent is selected from the group consisting of 1,1,2-trichloro-1,2,2-trifluoroethane and hexane.

6. The method of claim 1 wherein said surface tension is determined by the following procedure:
   (a) measuring the surface tension of said ink vehicle;
   (b) soaking said foam in said ink vehicle for a period of time;
   (c) measuring the surface tension of said ink vehicle following said soaking; and
   (d) comparing the surface tension of said ink vehicle prior to said soaking and following said soaking to determine whether said surface tension following said soaking is at least equal to or less than said about 40 dyne/cm or whether said drop in surface tension is greater than or less than said about 7 dyne/cm.

7. The method of claim 6 wherein said soaking is carried out at about 60° C. for about 4 days.

8. A method of determining cleanliness level in foams used as ink reservoirs and ink delivery systems in ink-jet printing to ensure sufficient removal of contaminants from said foams so as to provide ink stored in said foam with at least adequate ink fluid properties, said method comprising determining whether the amount of non-volatile residues is greater or less than about 0.2% by weight, with adequate ink fluid properties being associated with the lesser value.

9. The method of claim 8 wherein the amount of non-volatile residues is determined by the following procedure:
   (a) weighing at least one foam;
   (b) extracting said at least one foam in a solvent capable of extracting said non-volatile residues without attacking said foam;
   (c) evaporating said solvent and determining the weight of the residue remaining; and
   (d) comparing said weight with the weight of said at least one foam that was extracted to determine whether said amount is greater than or less than about 0.2% by weight.

10. The method of claim 9 wherein said solvent is non-azeotropic and non-polar.

11. The method of claim 10 wherein said solvent is selected from the group consisting of halo-hydrocarbons and hydrocarbons.

12. The method of claim 11 wherein said solvent is selected from the group consisting of 1,1,2-trichloro-1,2,2-trifluoroethane and hexane.

13. A method of determining cleanliness level in foams used as ink reservoirs and ink delivery systems in ink-jet printing on specially-coated paper to ensure sufficient removal of contaminants from said foam to provide ink stored in said foam with at least adequate ink fluid properties, said method comprising determining whether the surface tension of ink vehicle exposed to said foam is at least equal to or less than about 40 dyne/cm, with adequate ink fluid properties being associated with the former value, with said surface tension determined by the following procedure:
   (a) measuring the surface tension of said ink vehicle;
   (b) soaking said foam in said ink vehicle for a period of time;
   (c) measuring the surface tension of said ink vehicle following said soaking; and
   (d) determining whether said surface tension following said soaking is at least equal to or less than about 40 dyne/cm.

14. The method of claim 13 wherein said soaking is carried out at about 60° C. for about 4 days.

15. A method of determining cleanliness level in foams used as ink reservoirs and ink delivery systems in ink-jet printing on plain paper to ensure sufficient removal of contaminants from said foam to provide ink stored in said foam with at least adequate ink fluid properties, said method comprising determining whether the drop in surface tension of ink vehicle exposed to said foam is at least equal to or less than about 7 dyne/cm, with adequate ink fluid properties being associated with the lesser value.

16. The method of claim 15 wherein said surface tension is determined by the following procedure:
   (a) measuring the surface tension of said ink vehicle;
   (b) soaking said foam in said ink vehicle for a period of time;
   (c) measuring the surface tension of said ink vehicle following said soaking; and
   (d) comparing the surface tension of said ink vehicle prior to said soaking and following said soaking to determine whether said drop in surface tension is greater than or less than about 7 dyne/cm.

17. The method of claim 15 wherein said soaking is carried out at about 60° C. for about 4 days.

* * * * *